US009463160B2

(12) United States Patent
Yoo et al.

(10) Patent No.: US 9,463,160 B2
(45) **Date of Patent: *Oct. 11, 2016**

(54) DOSAGE FORM EXHIBITING RAPID DISPERSE PROPERTIES, METHODS OF USE AND PROCESS FOR THE MANUFACTURE OF SAME

(75) Inventors: Jaedeok Yoo, West Orange, NJ (US); Sandeep Kumar, Trenton, NJ (US); Donald C. Monkhouse, Radnor, PA (US)

(73) Assignee: Massachusetts Institute of Technology, Cambridge, MA (US)

(*) Notice: Subject to any disclaimer, the term of this patent is extended or adjusted under 35 U.S.C. 154(b) by 2863 days.

This patent is subject to a terminal disclaimer.

(21) Appl. No.: 10/200,029

(22) Filed: Jul. 19, 2002

(65) Prior Publication Data

US 2003/0133975 A1 Jul. 17, 2003

Related U.S. Application Data

(63) Continuation of application No. 09/027,183, filed on Feb. 20, 1998, now Pat. No. 6,471,992.

(60) Provisional application No. 60/038,883, filed on Feb. 20, 1997, provisional application No. 60/038,284, filed on Feb. 20, 1997.

(51) Int. Cl.

| | |
|---|---|
| ***A61K 9/00*** | (2006.01) |
| ***A61K 9/14*** | (2006.01) |
| ***A61F 13/15*** | (2006.01) |
| ***B27N 3/00*** | (2006.01) |
| ***B32B 17/00*** | (2006.01) |
| ***B29D 11/00*** | (2006.01) |
| ***B29C 35/04*** | (2006.01) |
| ***A61K 47/36*** | (2006.01) |
| ***A61K 9/20*** | (2006.01) |

(52) U.S. Cl.

CPC .......... *A61K 9/0056* (2013.01); *A61K 9/2072* (2013.01); *A61K 9/2095* (2013.01)

(58) Field of Classification Search

CPC . A61K 9/2095; A61K 9/2072; A61K 9/0056
USPC .................................. 424/484–85, 486, 488
See application file for complete search history.

(56) References Cited

U.S. PATENT DOCUMENTS

| | | | | |
|---|---|---|---|---|
| 4,642,903 A | | 2/1987 | Davies | |
| 4,855,326 A | | 8/1989 | Fuisz | |
| 4,990,535 A | * | 2/1991 | Cho et al. | 514/556 |
| 5,204,055 A | | 4/1993 | Sachs et al. | |
| 5,206,025 A | | 4/1993 | Courteille et al. | |
| 5,260,009 A | | 11/1993 | Penn | |
| 5,380,473 A | | 1/1995 | Bogue et al. | |
| 5,490,962 A | | 2/1996 | Cima et al. | |
| 5,503,785 A | | 4/1996 | Crump et al. | |
| 5,516,530 A | | 5/1996 | Lo et al. | |
| 5,518,730 A | | 5/1996 | Fuisz | |
| 5,560,926 A | * | 10/1996 | Franz et al. | 424/464 |
| 5,578,322 A | | 11/1996 | Shiozawa et al. | |
| 5,607,697 A | * | 3/1997 | Alkire et al. | 424/495 |
| 5,631,023 A | | 5/1997 | Kearney et al. | |
| 5,633,021 A | | 5/1997 | Brown et al. | |
| 5,653,925 A | * | 8/1997 | Batchelder | 264/113 |

OTHER PUBLICATIONS

C.W. Rowe et al. ("Multimechanism oral dosage forms fabricated by three dimensional printing" in J. Cont. Rel. (2000), 66, 11-17).

* cited by examiner

*Primary Examiner* — Sue Liu
*Assistant Examiner* — Helen Chui
(74) *Attorney, Agent, or Firm* — Rick Matos; Innovar, L.L.C.

(57) ABSTRACT

A rapidly dispersing dosage form is described. The dosage form releases its active ingredients within a period of less than about ninety seconds. These dosage forms exhibit a three-dimensional shape that is retained for adequate storage but is readily dispersed in the presence of excess moisture. Also disclosed are methods of administration of a medicament and a process for the preparation of rapidly dispersing dosage forms.

34 Claims, 2 Drawing Sheets

DOSAGE FORM EXHIBITING RAPID DISPERSE PROPERTIES, METHODS OF USE AND PROCESS FOR THE MANUFACTURE OF SAME

1. FIELD OF THE INVENTION

The present invention relates to rapidly dispersing dosage forms, also known as "flash dose" dosage forms. In particular, the pharmaceutical compositions of the present invention release their active ingredients within a period of less than about ninety seconds and are suitable for administration to a subject via a variety of routes, preferably by insertion into a body cavity or application to a moist body surface or open wound. The invention also relates to methods of administration of a medicament and a process for the preparation of rapidly dispersing dosage forms.

2. BACKGROUND OF THE INVENTION

Tablets and pills are well known. They are generally the preferred vehicles for oral administration of both prescription and over the counter medications. There are certain situations, however, in which the use of tablets or pills is undesirable. For example, individuals with laryngeal inflammation or esophageal disorders may have difficulty swallowing. In other cases there is no liquid available to aid swallowing. Small children often find it difficult to swallow pills and/or may choke in the attempt. An alternative to tablets and pills is the use of liquid medicaments, e.g., elixirs and syrups. Liquid medicaments have their own drawbacks, however, including imprecise dose measurement and, in the case of oral administration to young children, loss of some or all of the medicament via deliberate or accidental rejection.

An ideal alternative would be a solid dosage form that can be administered orally, which rapidly disperses in the mouth, and hence does not require great effort in swallowing. Such an idealized approach minimizes the possibility of rejection, if administered to a young child, and yet remains stable in composition and structure over a reasonable period of time, i.e., has adequate shelf life. Suitable rapidly dispersing dosage forms could also be used in other applications, including the treatment of wounds and other bodily insults and diseased states in which release of the medicament by externally supplied moisture is not possible.

There have been prior attempts to make stable and quick dispersing dosage forms. Effervescent dosage forms and quick release coatings of insoluble microparticles are described in U.S. Pat. Nos. 5,578,322 and 5,607,697. Freeze dried foams and liquids are described in U.S. Pat. Nos. 4,642,903 and 5,631,023. Melt spinning of dosage forms is described in U.S. Pat. Nos. 4,855,326, 5,380,473 and 5,518,730. Each of these dosage forms has drawbacks that limit their usefulness.

In particular, effervescent dosage forms, while providing rapid dissolution, require that a combination of an acid and an alkali be used. This limits the type of active ingredients (i.e., medicaments) which can be incorporated in the dosage form to those which are insensitive to acid or alkali levels. Moreover, the coating of microparticles may affect the oral release of the microparticles themselves, but not necessarily the oral release of the free form of the medicament contained in the microparticles.

Freeze-drying is a complex process and limits the scope of suitable medicaments to those having good solubility and relatively low density. Freeze dried dosage forms are also fragile and, hence, may require special handling and packaging. On the other hand, melt spinning requires that both medicament and a carrier be forced at high temperature and pressure through a small orifice, which requires the use of highly heat stable medicaments and results in a malleable amorphous product best described as a wool or fiber.

An alternative manufacturing processes is solid, free-form fabrication (SFF), which is a technique capable of creating complex structures via a layering process. One example of SFF is three-dimensional printing (3DP) which employs computer-aided design (CAD) to construct components in a sequential laminating process. U.S. Pat. No. 5,490,962 relates to the use of 3DP for the preparation of various medical devices. This patent is silent, however, and does not address the problems associated with oral administration under the situations described above, nor does it disclose, teach, or suggest the construction of rapidly dispersing dosage forms. It should be noted that this patent, as well as any other reference cited in the present specification, is incorporated by reference herein in its entirety.

Hence, there remains a need in the art for a convenient, pre-measured dosage form that is stable, and yet is suitable for oral administration to small children and others having difficulty in swallowing. There is also a need in the art for a dosage form suitable for placement in a non-oral body cavity, body surface, or exposed area which can effect rapid release of a medicament without the need of applying (i.e., without necessarily being accompanied by) externally supplied moisture. These needs are met by the dosage form of the present invention, as described further below.

3. SUMMARY OF THE INVENTION

It is accordingly an aspect of the invention to provide a rapidly dispersing dosage form suitable for placement in a body cavity, on a body surface or exposed area, such as an open wound.

It is another aspect of the invention to provide a rapidly dispersing dosage form that can disperse in less than about five minutes, preferably less than about ninety seconds, more preferably in less than about thirty seconds and most preferably in less than about ten or fifteen seconds.

It is yet another aspect of the invention to provide a rapidly dispersing dosage form that can incorporate a wide range of medicaments, and is not limited by processing considerations or composition requirements.

It is yet another aspect of the invention to provide a rapidly dispersing dosage form that can incorporate two or more medicaments either as a mixture or as separate domains within the dosage form.

It is yet another aspect of the invention to provide a rapidly dispersing dosage form having superior hardness and friability characteristics and which has a shelf life of at least about one year.

These aspects, and others set forth more fully below, including methods of administration of a medicament, processes for the preparation of certain rapidly dispersing dosage forms and drug delivery vehicles, are achieved by the present invention.

In particular, a rapidly dispersing dosage form is disclosed which comprises a solid matrix incorporating at least one active ingredient, the matrix having a three-dimensional structure suitable for administration to the subject, and wherein the matrix comprises a bulk material and a binder, the bulk material comprising at least one pharmaceutically acceptable compound in powder form, the binder comprising a substantially water-soluble pharmaceutically acceptable substance that together with the powdered compound allows the matrix to maintain its three-dimensional structure in the absence of excess moisture. The pharmaceutical composition of the present invention is designed to disintegrate with release of the one or more active ingredients within a time period ranging from about one to about ninety seconds after administration to the subject or upon contact with moisture. Such dosage forms also exhibit hardness and friability characteristics sufficient to provide a commercially acceptable shelf life, preferably a shelf life of at least about one year.

4. BRIEF DESCRIPTION OF THE DRAWINGS

5. DETAILED DESCRIPTION OF THE INVENTION

Figure 1:
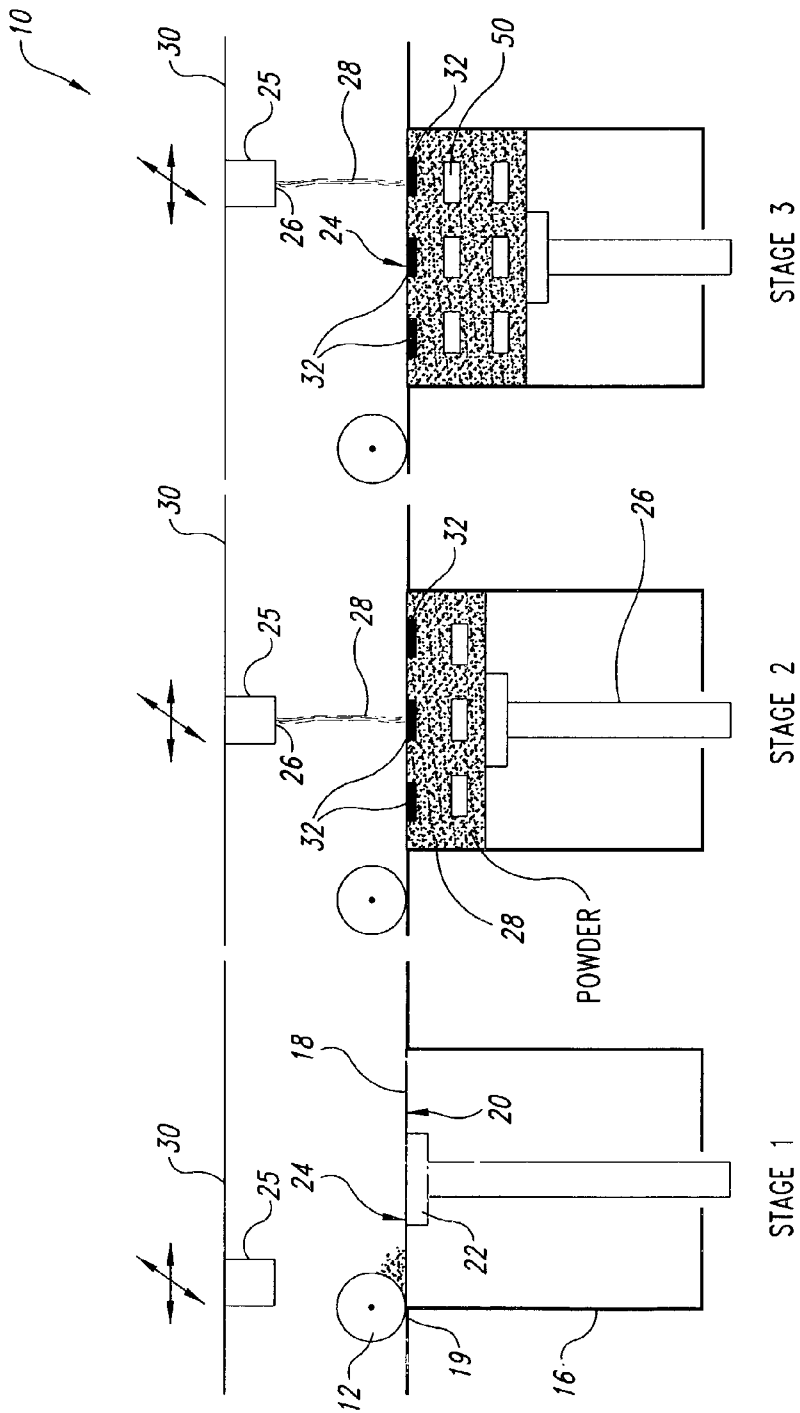
FIG. 1 is a schematic illustration of the process for forming a rapid release dosage form.

Solid, free-form fabrication (SFF) methods offer several unique opportunities for the construction of rapidly dispersing dosage forms. These dosage forms can be constructed with a matrix having a three-dimensional architecture, which is rapidly dispersed, disrupts, disintegrates, or otherwise dissolves substantially immediately. The unconventional dosage forms of the present invention are built through an SFF process, such as 3DP. The instructions for fabricating the dosage forms, which include all the necessary process parameters, are communicated via the computer that controls the operation of the 3DP machine.

Examples of useful SFF fabrication techniques include, but are not limited to ballistic particle manufacturing described by Brown et al., in U.S. Pat. No. 5,633,021, fusion deposition modeling described by Penn and Crump et al., in U.S. Pat. Nos. 5,260,009 and 5,503,785, or 3DP.

3DP is described by Sachs et al., in U.S. Pat. No. 5,204,055 and Cima et al., in U.S. Pat. No. 5,490,962. Suitable manufacturing devices include both those having a continuous jet print head and those having a drop-on-demand print head. Briefly, 3DP is used to create a solid object by printing fluid droplets, using either the continuous jet or the drop-on-demand print head, into selected areas of sequentially deposited layers of powder.

The present inventors have found that three-dimensional printing or 3DP is ideally suited for the preparation of rapidly dispersing (i.e., rapid release, disruption, disintegration, or dissolution within less than about ninety seconds, preferably thirty seconds, more preferably fifteen seconds, most preferably ten seconds) dosage forms. The ability of 3DP to build complex microstructural features within macroscopic structures allows the fabrication of hollow spaces within a device or vehicle, such as a solid (i.e., not a liquid) pharmaceutical dosage form.

Most pharmaceutically acceptable excipients, both small molecules and polymers, can be employed, which allow a pharmaceutically active ingredient to be loosely encased in a porous structure that is subject to rapid dispersion in the presence of an appropriate solvent (e.g., body fluids, including but not limited to blood, sweat, tears, saliva, semen, vaginal secretions, urine, plasma, puss and the like). Some of these excipients, suitable for use in the three-dimensional printing process of the invention, are listed in the Handbook of Pharmaceutical Excipients (Eds. A. Wade and P. J. Weller, Second edition, American Pharmaceutical Association, The Pharmaceutical Press, London, 1994).

The three-dimensional printing process, which can be used for the preparation of the rapidly dispersing dosage forms of the invention, is normally conducted at ambient temperatures. The process can utilize a variety of fluids, including biologically compatible organic and aqueous solvents. The process is additive, whereby microscopic features are incorporated layer by layer, allowing a wide range of possible architectures to be constructed precisely on a sub-millimeter scale. Using three-dimensional printing to control simultaneously both the microscopic features and the macroscopic shape, the unique drug delivery systems of the present invention are obtained.

Because 3DP is a solid, free-form (SFF) fabrication technique in which objects are built in a laminated fashion through sequential addition of patterned thin layers, it allows control over both structure and composition of the drug delivery systems of the present invention. This control is achieved at three levels: 1) macroscopic shapes (at the cm level); 2) intermediate features, such as size and orientation of pores and channels (at ~100 μm level); and 3) microscopic features, including porosity in the structural walls of the dosage form (at the ~10 μm level). The information needed to form these two-dimensional segments is obtained by calculating the intersection of a series of planes with a computer-aided design (CAD) rendition of the object. A schematic of a 3DP apparatus useful in carrying out the invention is illustrated by FIG. 1, wherein the apparatus is indicated generally by the number 10.

A powder spreader 12 is positioned adjacent the upper edge 14 of a powder box 16. The powder box 16 contains a layer of powder 18 supported by a base 20 and a movable piston 22. The upper surface 24 of the powder layer 18 is substantially flush with upper edge 14 of the powder box 16. Above the upper surface 14 and spaced therefrom is a printhead assembly 25 including a dispensing module 26 for dispensing a stream 28 of fluid droplets. The dispensing module 26 can be positioned in an x-y plane parallel to the upper surface 24 using an x-y positioning system, such as raster 30.

In operation, the powder spreader 12 spreads a thin layer of powder 18 into the box 16 to maintain a flush upper surface 24. The printhead assembly 25 then scans over the upper surface 24 and deposits droplets into selected regions 32 of upper surface 24. In the selected regions 32, the binder joins individual powder particles to form layers 24 containing solid regions, the thickness of which varies as a function of binder properties and the amount of fluid applied per unit area. Once the printhead assembly 25 has completed a scan, the floor of the powder box drops down, and a new layer of powder is spread. Information for the next layer is relayed from the computer and then printed. The process of spreading powder and depositing droplets is repeated until the desired number of layers for the dosage form is complete.

The total thickness of the dosage form will be a function of the number and thickness of the individual layers. The evaporation of solvent during the drying process leaves a matrix having a three-dimensional architecture comprising the bulk material bound by solidified binder and the other components, including one or more active ingredients and any optional pharmaceutically acceptable excipients.

The number of layers printed may be from 5 to 50. For a typical oral dosage form, the number of layers may vary from about 15 to about 25.

The freshly formed tablets are dried in the powder bed for a specified amount of time ranging from about 2 to about 48 hours, typically about 16 to about 24 hours. During the drying process, volatile material deposited with the fluid evaporates. Thereafter, the dried tablets are separated from the loose powder by hand for small batches. Mechanical means for harvesting tablets may also be used. Finally, a completed dosage form 50 is obtained.

Figure 2:
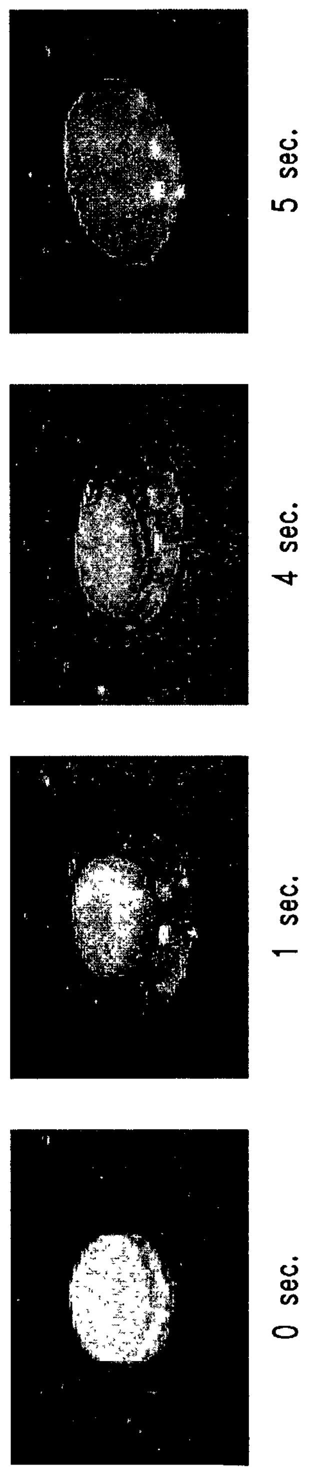
FIG. 2 is a set of photographs illustrating a completed dosage form and various stages of its dispersion upon contact with water.

FIG. 2 shows the photographs of a completed dosage form and its stages of dispersion upon contact with 500 μL of water. During the first second, the dosage form absorbs water, followed by a rapid dispersion that is completed within 5 seconds.

The following are the preferred parameters for the manufacture of rapid release dosage forms using a continuous jet printhead. A layer of powder is spread 100-300 μm deep, typically about 200 μm. The printhead scans at a rate of about 0.5 to 3.0 m/sec, and most preferably at about 1.75 m/sec. The size of the fluid droplets delivered by the printhead ranges from about 15 μm to about 150 μm in diameter. The flow rate of the fluid delivered by the print head varies from about 0.2 to about 3.0 mL/min, preferably about 0.8 to about 1.2 mL/min. The spacing between the parallel lines of printing range from 20 to about 1000 μm, and typically are 100 to 200 μm.

Similarly, manufacture of rapidly dispersing dosage forms using drop-on-demand print head apparatus can be achieved using the following parameters. The layer of powder is spread 100-500 μm deep, typically about 250 μm. The printhead scans at a rate of 0.1 to 1 m/sec, most preferably at about 0.5 m/sec. The printhead delivers droplets of about 50 μm to about 500 μm in diameter. The flow rate of the fluid delivered by the printhead is from about 0.2 to about 3 mL/min, preferably about 1 to about 1.5 mL/min. The spacing between parallel lines of printing ranges from about 100 to about 1500 μm, and typically are about 500 to 750 μm.

In general, two components are used to construct the matrix of the rapidly dispersing dosage forms. The first component is the powder material to be spread in layers. The second component is the fluid (in some cases the fluid may also be a binder or contain a binder) that is dispensed by the printhead. The powder material is comprised of one or more pharmaceutically acceptable bulk materials, one or more binders, one or more and actives, or optional excipient(s). The fluid dispensed is a pharmaceutically acceptable solvent or combination of solvents and may contain one or more binders and actives. Suitable solvents include water, an alcohol, such as ethanol or methanol and the like.

To make dosage forms, the bulk powder materials include, but are not limited to, spray dried lactose, fructose, sucrose, dextrose, sorbitol, mannitol, xylitol, and microcrystalline cellulose.

The binder is an essential element of the invention, as it produces adhesion between particles of the powder and binder material. It is this adhesion that enables the dosage form to maintain characteristics of hardness and friability adequate to permit handling and storage.

The term adhesion means the bonding or binding of particles of the bulk material to each other or to particles of the binder. The binder can be a solvent for the bulk material or a further substance that is capable of bonding to particles of the bulk compound. The strength and extent of the binding depends on the proportion of the binder either in the powder layer or dissolved in the solvent, and is a function of the amount of fluid deposited.

The binder may be included in either the powder material or in the fluid dispensed through the printhead. Adhesion of the particles to and/or by the binder occurs either when the binder is contacted by the fluid from the printhead or when it is present (i.e., soluble) in the fluid. Suitable binder materials include, but are not limited to, arabinogalactan, polyvinylpyrrolidone, sorbitol, mannitiol, xylitol and the like.

The proper placement of droplets can be used to control the local composition and to fabricate components with true three-dimensional compositional gradients.

Dosage forms fabricated using 3DP are capable of releasing a large variety of therapeutic agents. The dosage forms of the present invention may contain pharmaceutical agents in quantities ranging from micrograms to hundreds of milligrams depending on (1) the physical and chemical properties of the drug, (2) the choice of bulk powder material, binder and solvent combination, and (3) the overall size and shape of the device. Examples of agents deliverable by the dosage forms of the present invention include nonprescription pharmaceuticals, prescription pharmaceuticals, and other molecules exhibiting biological activity, such as vitamins or nutrients.

In a preferred embodiment, the dosage forms of the instant invention incorporate agents commonly used for relief of symptoms of the common cold or sleep aids. Such agents include, but are not limited to, chlorpheniramine maleate, pseudoephedrine hydrochloride, diphenhydramine hydrochloride, doxylamine succinate, dextromethorphan hydrobromide, acetaminophen, or combinations thereof.

The compositions of the present invention, being manufactured with precise dosage but not constrained to a particular physical dimension, can be further used in other than the oral cavity. Any natural or unnaturally occurring cavity, such as resulting from traumatic injury or surgical intervention, may be a target site for premeasured dosage delivery through contact with the dosage forms of the present invention.

The dosage forms of the present invention may be further shaped to facilitate assembly into a device that is designed for placement on the body of a mammal. One such embodiment may be a wafer-like shape intended for topical placement and affixed to an adhesive patch or strip.

Hence, the present invention provides a pharmaceutical composition suitable for administration to a subject comprising one or more active ingredients and a rapidly dispersing, non-compressed solid matrix harboring the one or more active ingredients, the matrix having a three-dimensional shape and comprising a bulk material and a binder, the bulk material comprising a pharmaceutically acceptable compound in particulate form and the binder comprising a pharmaceutically acceptable, substantially water-soluble substance having the capacity to adhere to and bind together the particles of the bulk material, to maintain the three-dimensional shape of the matrix in the absence of moisture and to permit the composition to exhibit hardness and friability characteristics adequate for storage and handling. In particular, the instant composition exhibits a three-dimensional shape that is disrupted within a time period of less than about ninety seconds upon contact of the composition with moisture, with release of the one or more active ingredients to the subject. Preferably, the time period within which the composition of the invention is dispersed in less than about sixty seconds, more preferably less than about thirty seconds, most preferably less than about fifteen, ten, or five seconds.

In a particular embodiment of the invention, the composition of interest is further characterized as exhibiting a bulk density ranging from about 150 (mg/mL) to about 1300 (mg/mL), preferably from about 400 (mg/mL) to about 1000

(mg/mL). Moreover, preferred compositions of the invention can be characterized as exhibiting a porosity ranging from about 10% to about 90% of the dosage form volume, preferably from about 30% to about 70% of the dosage form volume.

Other characteristics of the compositions of the invention include a hardness ranging from about 1.0 kp to about 20 kp, preferably from about 3 kp to about 10 kp, a friability of less than about 25%, preferably less than about 10%.

Depending on the applications sought, the pharmaceutical composition of the invention exhibit a three-dimensional shape that is dispersed within the desired time period upon contact of the composition with moisture found in a subject's body cavity, including the mouth, the eye, the nose, the vagina, the rectum and open wounds. Also, a wide variety of substances can be used as the bulk material and the binder, including water-soluble synthetic polymers. (The bulk material and the binder may even comprise the same water-soluble synthetic polymer, such as polyvinylpyrrolidone). Preferably, the bulk material comprises spray dried lactose and the binder comprises polyvinylpyrrolidone.

Also contemplated is a method of administering a medicament comprising one or more active ingredients to a subject. The steps of the method comprises (a) providing a rapidly dispersing, non-compressed dosage form of the medicament, the dosage form comprising a pharmaceutically acceptable solid matrix including a compound in powder form, the particles of which are bound together by a binder, and (b) inserting the dosage form into a moisture-containing body cavity, the moisture being capable of dissolving the binder and dispersing the dosage form within a time period ranging from about one to about ninety seconds, with release of the medicament to the body cavity of the subject.

The method of administering a medicament may also comprise applying the dosage form on a moist body surface, the moisture on the moist body surface being capable of dissolving the binder and dispersing the dosage form within a time period ranging from about one to about ninety seconds, with release of the medicament to the body surface of the subject.

Accordingly, it should be evident that the invention also contemplates a process for the preparation of a rapidly dispersing solid dosage form comprising one or more active ingredients, comprising the steps of: (a) providing a pharmaceutically acceptable powdered compound, a pharmaceutically acceptable binder and one or more active ingredients, together with any optional pharmaceutically acceptable excipients; (b) combining the compound, binder, one or more active ingredients and optional excipients using a solid, free-form fabrication technique to provide a non-compressed solid dosage form having a three-dimensional shape, the solid dosage form able to maintain its three-dimensional shape in the absence of moisture and to exhibit hardness and friability characteristics adequate for storage and handling, and provided that the solid dosage form is dispersed within a time period of less than about ninety seconds upon contact of the solid dosage form with moisture, with release of the one or more active ingredients. Such active ingredients may further include a taste masking agent, a salivary gland stimulant, a breathe refresher, or a nasal decongestant.

6. EXAMPLES

The following examples are set forth herein to further describe the invention, including methods for manufacturing the rapidly dispersing dosage forms.

6.1. Rapidly Dispersing Dosage Forms Containing Lactose

The following experiments are carried out to demonstrate the feasibility of manufacturing rapidly dispersing oral dosage forms using a combination of lactose and microcrystalline cellulose (MCC).

Device Design

The program specifies 170 μm line spacing and speed variable conditions between four different rows of tablets; velocities vary between 0.75, 1.0, 1.25, or 1.5 m/sec. The flow rate is maintained at 1.22 mL per min.

A 20-layer tablet is printed with the dimensions of 1 cm in diameter and 3.5 mm in height.

Materials and Manufacturing Process

Two powder mixtures are used, the compositions of which are shown in Table 1, below; the fluid is distilled water. In these compositions, a combination of lactose (a water soluble carbohydrate) and microcrystalline cellulose (a water insoluble polymer) is used as the bulk powder material, comprising more than 50% by weight of the final composition of the tablet. The powder material also includes a binder, such as starch or arabinogalactan. The deposition of water droplets from the printhead onto the powder layers facilitates the interparticle adhesion.

TABLE 1

| Ingredient | Powder Mix 1 | Powder Mix 2 |
|---|---|---|
| Lactose Monohydrate | 472 mg | 472 mg |
| Microcrystalline cellulose | 140 mg | 140 mg |
| Starch | 70 mg | |
| Arabinogalactan | | 70 mg |

Analysis of Product

The tablets produced above disintegrate in 12 seconds in 100 μL of water.

The dimensions and weight of the tablets are shown in Table 2.

Several manufacturing runs are conducted in which the same printing parameters are used but the composition and source of the bulk material are varied.

TABLE 2

| Formulation* | Composition | Diameter (cm) | Height (cm) | Average Weight (n = ?) | Volume (cc) | Density (g/cc) |
|---|---|---|---|---|---|---|
| LMA01 | 70:20:10 | 1.11 | 0.599 | 0.3865 | 0.5796 | 0.667 |
| LMA02 | 70:20:10 | 1.10 | 0.5951 | 0.3302 | 0.5655 | 0.584 |
| LMA03 | 62:18:12 | 1.121 | 0.507 | 0.3773 | 0.5004 | 0.754 |
| LMA04-01 | 62:18:12 | 1.001 | 0.512 | 0.3774 | 0.4029 | 0.937 |
| LMA04-02 | 62:18:12 | 1.011 | 0.521 | 0.3904 | 0.4182 | 0.933 |

*L = lactose monohydrate,
M = microcrystalline cellulose, and
A = arabinogalactan.

The mechanical properties of the various compositions are analyzed for their resistance to breaking using the tablet friability test (USP protocol <1216>). The term friability is the tendency to lose material from the outer edges and surfaces upon mechanical insult. The test employs a drum having the dimensions of 285 mm in diameter and 39 mm deep (VanKel Industries, Inc. Edison, N.J.) which is rotated at 25 rpm for 100 revolutions. A minimum number of 20 tablets are tumbled at each revolution by a curved projection that extends from the middle of the drum to the outer wall. Thus, at each turn the tablets are caused to roll or slide and fall about 130 mm onto the drum or each other. All loose powder is removed from the tablets and they are weighted collectively before and after the 100 revolutions.

The strength or hardness of the tablets is measured by a fracture test. A VK200 Tablet Hardness Tester (VanKel Industries, Edison, N.J.) is used. A tablet is centered between the jaws of the tester and force is applied until the tablet fractures. The load at fracture is returned in kiloponds (kp). A kilopond is a metric unit of force measurement with 1 kp being equivalent to 9.807 Newtons.

TABLE 3

| Formulation | Average Weight (n = 20) | Weight Uniformity (% RSD) | Friability (%) | Hardness (Kp) |
|---|---|---|---|---|
| LMA01 | 0.3865 | 5.52 | 3.00 | 1.35 |
| LMA02 | 0.3302 | 3.62 | 7.24 | 1.03 |
| LMA03 | 0.3773 | 3.05 | 3.61 | 5.63 |
| LMA04 | 0.3904 | 1.43 | 1.92 | 8.50 |

The resulting tablets have the property of rapidly dispersing and exhibit hardness and friability sufficient to be handled and stored. Tablets containing microcrystalline cellulose dispersed rapidly, but apparently because of the insolubility of the microcrystalline cellulose leave fine particles in solution. These cellulose particles may be deemed undesirable in an oral dosage form, however.

6.2. Rapidly Dispersing Dosage Forms Containing Arabinogalactan or Sorbitol as Binder

Materials and Manufacturing Process

Combinations using MCC as the bulk powder material and aqueous solutions of arabinogalactan or sorbitol are tested in a pre-manufacturing test wherein dried mixtures of the powders which have been previously partially wetted with aqueous arabinogalactan or sorbitol solution are subjected to a dissolution in 50 μL of water. These experiments demonstrate that aqueous solutions of both arabinogalactan and sorbitol are suitable binding agents when deposited through the printhead.

6.3. Rapidly Dispersing Tablets Containing Polyvinylpyrrolidone Deposited as Part of the Fluid Dispensed from the Printhead Another strategy involves including a binding agent in solution in the fluid. This binder solution may be used for printing on lactose powder alone or a powder blend containing lactose and a further binding agent. The binding agent in the binder solution may be that same as the one in the powder or it may be different. Inclusion of the binding agent in the binder solution will result in a different internal microstructure of the tablets, particularly the pore size. Upon printing, as the solvent evaporates, it will leave behind a solid residue of the binding agent, which will occupy the void space in-between the powder particles. The resulting structure will have higher density compared to tablets fabricated without the binding agent in the binder solution. This is illustrated in the following example using polyvinylpyrrolidone (Kollidon 25) as the binder material both in the powder and in the fluid.

| Materials and Methods | |
|---|---|
| Powder: | 95:5 mixture of lactose:Kollidon 25 |
| Binder: | 20% (wt./vol.) Kollidon 25 in a solvent comprising 50:50 ethanol and water |
| Binder flow rate: | 1.2 mL/min |
| Layer thickness: | 200 μm |
| Line spacing: | 170 μm |
| Number of layers: | 18 |
| Stencil hole diameter: | 1 cm |
| Print speeds: | 1.00, 1.25, 1.50, 1.75 and 2.00 m/s |

An increase in the print speed from 1.0 m/s to 2.0 m/s reduces the total volume of binder solution deposited in the tablets by half. From Table 4, it can be seen that as the print speed increases, the bulk density (theoretical, calculated from the weight and dimensions of the tablet) decreases. A simultaneous decrease in the dimensions and weight of the tablets is also seen. This decrease is attributed to the fact that a decrease in the total volume of binder droplets deposited onto the powder results in a decrease in the extent of binder solution spreading in the powder. As expected, reducing the print speed also decreases the flash time and the hardness and increases the friability of the tablets. This result is obtained because the proportion of Kollidon 25 decreases in the tablets as the print speed increases (see Table 5).

TABLE 4

| Physical Properties of the Tablets (Average of 5 Tablets) | | | | | | | |
|---|---|---|---|---|---|---|---|
| Speed | Diameter (cm) | Height (cm) | Weight (g) | Bulk Density (g/cm3) | Flash time(s) | Hardness (kp) | Friability (%) |
| 1.25 | 1.11 | 0.410 | 0.262 | 0.658 | 5.63 | 3.1 | 14.5 |
| 1.5 | 1.06 | 0.409 | 0.230 | 0.635 | 5.06 | 2.8 | 17.2 |
| 1.75 | 1.04 | 0.399 | 0.208 | 0.613 | 4.30 | 2.3 | data not available |
| 2 | 1.03 | 0.381 | 0.185 | 0.584 | 3.61 | 1.7 | 21.7 |

TABLE 5

| Composition of the Tablets | | | |
|---|---|---|---|
| Print Speed | Kollidon 25 (g) | Lactose (g) | Kollidon/Lactose ratio |
| 1.25 | 0.0384 | 0.2236 | 0.172 |
| 1.5 | 0.0326 | 0.1974 | 0.165 |
| 1.75 | 0.0284 | 0.1796 | 0.1583 |
| 2 | 0.0250 | 0.1600 | 0.157 |

From Table 6, it can be seen that an increase in the print speed also increases the void volume inside the tablets, as illustrated by an increase in the percent volume of the tablets penetrated by mercury at 30 psi (% intrusion).

TABLE 6

Mercury Porosimetry Data (Average of 2 Tablets)

| Print speed (m/s) | Weight (g) | Weight-normalized Intrusion volume (ml/g) | Bulk density (g/mL) | Measured volume (ml) | Intrusion volume (ml) | % Intrusion |
|---|---|---|---|---|---|---|
| 1 | 0.275 | 0.515 | 0.821 | 0.335 | 0.142 | 42.282 |
| 1.25 | 0.2455 | 0.568 | 0.7815 | 0.3145 | 0.139 | 44.389 |
| 1.5 | 0.2195 | 0.585 | 0.771 | 0.285 | 0.128 | 45.104 |
| 1.75 | 0.1835 | 0.601 | 0.759 | 0.242 | 0.110 | 45.616 |
| 2 | 0.173 | 0.6215 | 0.754 | 0.229 | 0.108 | 46.861 |

6.4. Rapidly Dispersing Tablets with Varying Architecture in Different Layers A slightly more complex strategy involves fabrication of tablets by varying the amount of binder deposited between different layers or within different predefined regions within the same layers. This tactic helps create sections within a tablet with different mechanical properties. This approach is used to design tablets in which the composition of the top and bottom layers is different from the middle layers. The following is an example of such a design in which two different grades of polyvinylpyrrolidone are used (Kollidon 25 and Plasdone C-15).

Each tablet is designed to contain 30 mg pseudoephedrine hydrochloride and 2 mg chlorpheniramine maleate.

| | |
|---|---|
| Powder: | 96:4 mixture of lactose:Kollidon 25 |
| Binder 1: | 200 g/L Plasdone C-15 in water, used for double printing the top and bottom 2 layers |
| Binder 2: | Solution containing 341 g/L pseudoephedrine hydrochloride, 22.73 g/L chlorpheniramine maleate, and 50 g/L Plasdone C-15 (polyvinylpyrrolidone K-15) solution in DI water, used for single printing the middle 14 layers. |
| Binder flow rate: | 1.0 mL/min |
| Layer thickness: | 200 μm |
| Line spacing: | 170 μm |
| Number of layers: | 18 |
| Stencil hole diameter: | 1.2 cm |
| Print speeds: | 1.75 m/s |

The physical properties of ten sample tablets are shown in Table 7 below.

TABLE 7

| Property | Average Value | Std Dev, (n = 10) |
|---|---|---|
| Diameter (mm) | 12.59 | 0.16 |
| Height (mm) | 4.25 | 0.10 |
| Weight (g) | 0.359 | 0.02 |
| Bulk Volume (ml) | 0.528 | 0.02 |
| Bulk Density (g/ml) | 0.68 | 0.02 |
| Hardness (kp) | 3.50 | 0.97 |
| Flash time (sec) | 4.37 | 0.66 |

This design allows the tablets to have stronger top and bottom layers, thereby increasing hardness and reducing friability, and a large middle portion with lower hardness, which enables the tablet to disperse rapidly. The drug content averages 99.2±1.3% for pseudoephedrine hydrochloride and 97.7±1.1% for chlorpheniramine maleate of the expected values, respectively.

It should be apparent to those of ordinary skill from the descriptions provided that other embodiments of the invention can be contemplated that are not specifically disclosed herein but which nonetheless conform to the scope and spirit of the present invention. Thus, the present invention should not be construed as being limited in any way by the specific embodiments provided herein, which invention is limited solely by the claims that follow.

What is claimed is:

1. A rapid release drug delivery system comprising: a non-compressed solid matrix having a three dimensionally printed architecture, the matrix comprising a bulk powder material, a water soluble binder and at least one active ingredient, and the active ingredient being present in one or more predetermined printed pattern within the matrix, wherein the matrix disperses in about 90 seconds or less upon contact with moisture thereby releasing the active ingredient, the matrix has a hardness of about 1 to about 20 kp, and the drug delivery system has a porosity of 10%-90%, wherein the matrix is prepared according to the process comprising:

a) providing one or more layers comprising a mixture of bulk powder material and a water soluble binder;

b) according to the one or more predetermined patterns, applying binding fluid to the one or more layers using a three-dimensional printing technique, the binding fluid comprising a pharmaceutically acceptable solvent and at least one active ingredient, or comprising a mixture of a pharmaceutically acceptable solvent and at least one active ingredient and water soluble pharmaceutically acceptable binder; and c) evaporating the solvent to provide a rapidly dispersing non-compressed solid matrix.

2. A rapid release drug delivery system comprising at least one active ingredient in a dispersing non-compressed solid matrix harboring the at least one active ingredient, the matrix comprising a bulk powder material and a water soluble binder, wherein the matrix has a structure of layers with programmed placement of binder printed within each layer, wherein the matrix is dispersed within a time period of about ninety seconds or less upon contact of the matrix with moisture thereby releasing the at least one active ingredient, the matrix has a hardness of about 1 to about 20 kp, and wherein the drug delivery system has a porosity of 10%-90%, wherein the matrix is prepared according to a process comprising:

a) providing one or more layers comprising a mixture of bulk powder material and at least one active ingredient;

b) according to the one or more predetermined patterns, applying binding fluid to the one or more layers using a three-dimensional printing technique, the binding fluid: comprising a mixture of water soluble binder and pharmaceutically acceptable solvent; or comprising a mixture of at least one active ingredient, pharmaceutically acceptable solvent and water soluble binder, and c) evaporating the solvent to provide the dispersing non-compressed solid matrix.

3. A pharmaceutical composition comprising:

a dispersing non-compressed solid matrix comprising a bulk powder material, a water soluble binder material and one or more active ingredients, wherein:

at least one of the binder material and/or the one or more active ingredients are three-dimensionally printed within the matrix according to one or more predetermined patterns, wherein the matrix has a hardness of about 1 to about 20 kp, the pharmaceutical composition has a porosity of 10%-90%, and the composition disperses within about ninety seconds upon contact of said composition with moisture, wherein:

a) the matrix is made according to a process comprising:

a1) providing one or more layers comprising a mixture of bulk powder material and water soluble binder material;

a2) according to the one or more predetermined patterns, applying binding fluid to the one or more layers using a three-dimensional printing technique, the binding fluid comprising a mixture of at least one active ingredient, pharmaceutically acceptable solvent and water soluble binder, and a3) evaporating the solvent to provide the dispersing non-compressed solid matrix; or b) the matrix is made according to a process comprising:

b1) providing one or more layers comprising a mixture of bulk powder material and at least one active ingredient;

b2) according to the one or more predetermined patterns, applying binding fluid to the one or more layers using a three-dimensional printing technique, the binding fluid comprising a mixture of water soluble binder and pharmaceutically acceptable solvent; or comprising a mixture of water soluble binder, pharmaceutically acceptable solvent and at least one active ingredient; and b3) evaporating the solvent to provide a rapidly dispersing non-compressed solid matrix.

4. The pharmaceutical composition of claim 3, wherein the matrix has three dimensionally printed compositional gradients.

5. The pharmaceutical composition of claim 3, wherein the water soluble binder comprises a pharmaceutically acceptable, substantially water-soluble substance having the capacity to adhere to and bind together the particles of said bulk powder material, to maintain the three-dimensional shape of said matrix in the absence of moisture and to permit said composition to exhibit hardness and friability characteristics adequate for storage and handling.

6. The pharmaceutical composition of claim 3 wherein the bulk powder material comprises a pharmaceutically acceptable compound and further comprises one or more binders, one or more actives, or one or more excipients.

7. The pharmaceutical composition of claim 3 wherein the dispersing matrix consists essentially of lactose and polyvinyl pyrrolidone and one or more of the active ingredients dispersed in said matrix; wherein:

said one or more of the active ingredients dispersed in said matrix is a taste masking agent, and wherein the binder material is printed in a predetermined pattern within the matrix.

8. The pharmaceutical composition of claim 3, wherein the moisture is a bodily fluid.

9. The pharmaceutical composition of claims 3, wherein the composition comprises two different active ingredients.

10. The pharmaceutical composition of claim 3, wherein the composition possesses a bulk density of ranging from about 150 mg/mL to about 1300 mg/mL.

11. The pharmaceutical composition of claim 3, wherein bulk powder material is selected from the group consisting of spray-dried lactose, fructose, sucrose, dextrose, sorbitol, mannitol, xylitol, microcrystalline cellulose and a combination thereof.

12. The pharmaceutical composition of claim 3, wherein the water soluble binder is selected from the group consisting of arabinogalactan, polyvinylpyrrolidone, sorbitol, mannitol, xylitol and a combination thereof.

13. The pharmaceutical composition of claim 3, wherein the one or more active ingredients is selected from the group consisting of chloropheniramine maleate, pseudoephedrine hydrochloride, diphenhydramine hydrochloride, doxylamine succinate, dextromethorphan hydrobromide, acetaminophen, or mixtures thereof.

14. The pharmaceutical composition of claim 3, wherein each of the bulk powder material and binder comprises a water soluble compound.

15. The pharmaceutical composition of claim 14, wherein the bulk powder material and binder comprise the same water soluble compound.

16. The pharmaceutical composition of claim 15, wherein the water soluble compound comprises polyvinyl pyrrolidone.

17. The pharmaceutical composition of claim 3, wherein the active ingredient is a taste masking agent, a salivary gland stimulant, a breathe refresher, or a nasal decongestant.

18. The pharmaceutical composition of claim 3, wherein the composition disrupts in less than about sixty seconds upon contact of said composition with moisture.

19. The pharmaceutical composition of claim 3, wherein the composition disrupts in less than about thirty seconds upon contact of said composition with moisture.

20. The pharmaceutical composition of claim 3, wherein the composition disrupts in less than about fifteen seconds upon contact of said composition with moisture.

21. The pharmaceutical composition of claim 3, wherein the composition disrupts in less than about ten seconds upon contact of said composition with moisture.

22. The pharmaceutical composition of claim 3, wherein the composition disrupts within five seconds upon contact of said composition with moisture.

23. The pharmaceutical composition of claim 3, wherein the composition has a porosity ranging from about 30% to about 70%.

24. The pharmaceutical composition of claim 3, wherein the composition possesses a bulk density ranging from about 400 mg/mL to about 1000 mg/mL.

25. The pharmaceutical composition of claim 3, wherein the composition disrupts in less than about thirty seconds upon contact of said composition with moisture; the composition has a porosity ranging from about 30% to about 70%; and the composition possesses a bulk density ranging from about 400 mg/mL to about 1000 mg/mL.

26. The drug delivery system of claim 1, wherein the matrix disrupts in less than about thirty seconds upon contact of said system with moisture; the matrix has a porosity ranging from about 30% to about 70%; and the matrix possesses a bulk density ranging from about 400 mg/mL to about 1000 mg/mL.

27. The drug delivery system of claim 2, wherein:

the matrix disrupts in less than about thirty seconds upon contact of said system with moisture; the matrix has a porosity ranging from about 30% to about 70%; and the matrix possesses a bulk density ranging from about 400 mg/mL to about 1000 mg/mL.

28. The pharmaceutical composition of claim 4, wherein:

the matrix disrupts in less than about thirty seconds upon contact of said composition with moisture; the matrix has a porosity ranging from about 30% to about 70%; and the matrix possesses a bulk density ranging from about 400 mg/mL to about 1000 mg/mL.

29. The pharmaceutical composition of claim 5, wherein: the matrix disrupts in less than about thirty seconds upon contact of said composition with moisture; the matrix has a porosity ranging from about 30% to about 70%; and the matrix possesses a bulk density ranging from about 400 mg/mL to about 1000mg/mL.

30. The drug delivery system of claim 1, wherein the matrix has a hardness of about 3 to about 10 kp.

31. The drug delivery system of claim 2, wherein the matrix has a hardness of about 3 to about 10 kp.

32. The pharmaceutical composition of claim 4, wherein the matrix has a hardness of about 3 to about 10 kp.

33. The pharmaceutical composition of claim 5, wherein the matrix has a hardness of about 3 to about 10 kp.

34. The pharmaceutical composition of claim 3, wherein the matrix has a hardness of about 3 to about 10 kp.

* * * * *